(12) United States Patent
D'Ambrosio

(10) Patent No.: US 6,459,760 B1
(45) Date of Patent: Oct. 1, 2002

(54) APPARATUSES AND METHODS FOR NON-DESTRUCTIVE INSPECTION

(75) Inventor: Karl V. D'Ambrosio, Seattle, WA (US)

(73) Assignee: Exotic Metals Forming Company, Inc., Kent, WA (US)

( * ) Notice: Subject to any disclaimer, the term of this patent is extended or adjusted under 35 U.S.C. 154(b) by 0 days.

(21) Appl. No.: 09/732,238

(22) Filed: Dec. 7, 2000

Related U.S. Application Data

(60) Provisional application No. 60/221,848, filed on Jul. 28, 2000.

(51) Int. Cl.[7] .............................................. G01B 15/00
(52) U.S. Cl. ........................... 378/43; 378/58; 378/195; 378/196; 378/207; 356/625; 356/634; 356/635
(58) Field of Search ........................... 378/58, 195, 196, 378/206, 208, 43; 356/614, 623, 621, 625, 634, 635

(56) References Cited

U.S. PATENT DOCUMENTS

| | | | | |
|---|---|---|---|---|
| 3,743,845 A | * | 7/1973 | Rabodzei et al. | 378/43 |
| 3,818,233 A | * | 6/1974 | Rabodzei et al. | 378/43 |
| 3,846,632 A | * | 11/1974 | Rabodzei et al. | 378/43 |
| 4,426,726 A | * | 1/1984 | Cheetham | 378/206 |
| 4,836,671 A | * | 6/1989 | Bautista | 356/3.1 |
| 4,989,225 A | * | 1/1991 | Gupta et al. | 378/10 |
| 5,119,408 A | * | 6/1992 | Little et al. | 378/4 |
| 5,521,957 A | * | 5/1996 | Hansen | 378/198 |
| 5,666,392 A | * | 9/1997 | Ploetz | 378/39 |
| 6,064,717 A | | 5/2000 | Ortega et al. | |
| 6,104,776 A | * | 8/2000 | Oikawa | 378/22 |
| 6,148,058 A | * | 11/2000 | Dobbs | 378/19 |
| 6,213,638 B1 | * | 4/2001 | Rattner | 378/198 |
| 2001/0005410 A1 | * | 6/2001 | Rasche et al. | 378/197 |

* cited by examiner

Primary Examiner—Robert H. Kim
Assistant Examiner—Allen C. Ho
(74) Attorney, Agent, or Firm—Perkins Coie LLP

(57) ABSTRACT

An automated real-time, non-destructive inspection system usable to inspect a selected structure for a defect and visually identify a defect's location. In one embodiment, the inspection system is an x-ray inspection system mounted to an articulatable robot arm movable relative to the selected structure. A support system is attached to the articulatable robot arm that supports an imaging source on a first support portion and a detector panel on a second support portion spaced apart from the first support portion. A visual targeting system configured to identify where an imaging beam axis intersects the selected structure is positioned adjacent to the imaging source. The inspection system is configured to maneuver the imaging source and detector panel around the selected structure such that the desired areas on the selected structure may be fully inspected without having to reposition the selected structure.

6 Claims, 6 Drawing Sheets

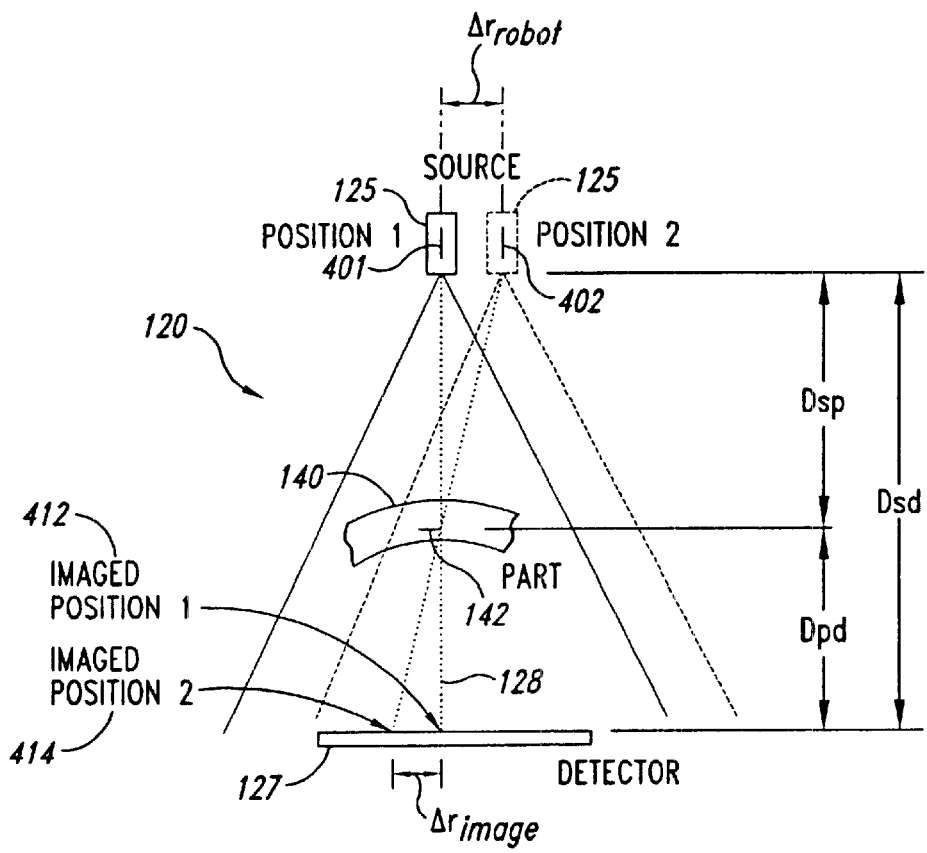
*Fig. 6*
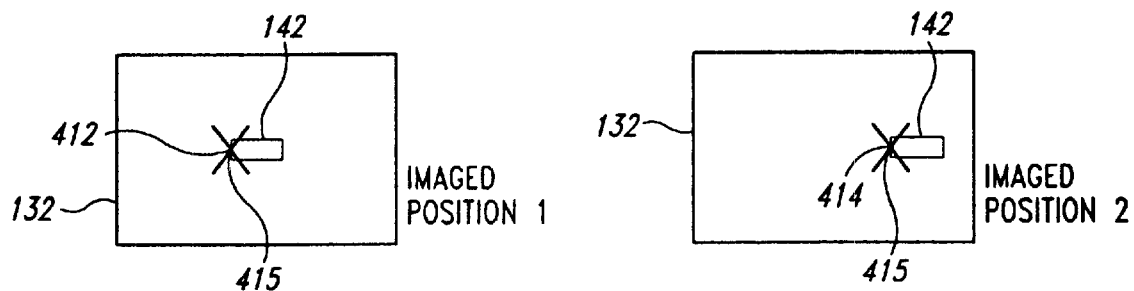
*Fig. 7*  *Fig. 8*

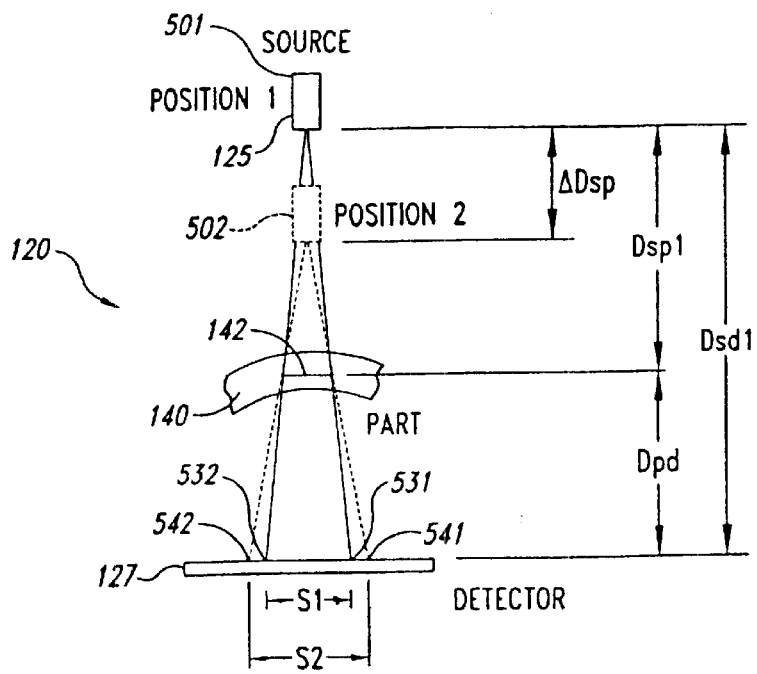
*Fig. 12*
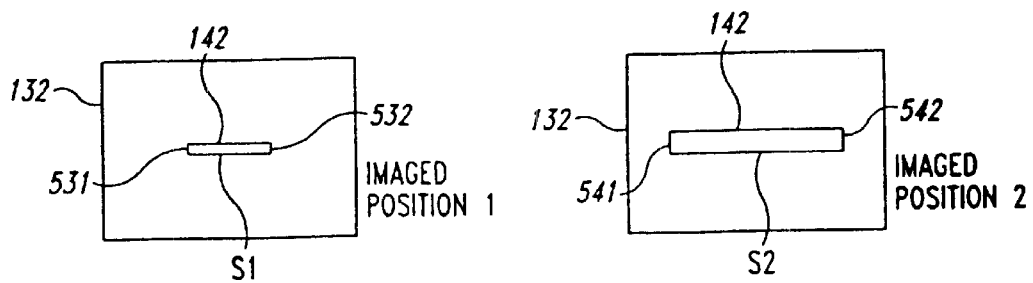
*Fig. 13*  *Fig. 14*

APPARATUSES AND METHODS FOR NON-DESTRUCTIVE INSPECTION

CROSS-REFERENCE TO RELATED APPLICATIONS

This application claims priority from United States Provisional Application No. 60/221,848 filed on Jul. 28, 2000 which is incorporated herein by reference.

TECHNICAL FIELD

The present invention is directed to apparatuses and methods for non-destructive inspection, and more particularly, to automated real-time, non-destructive inspection apparatuses and methods.

BACKGROUND OF THE INVENTION

Real-time x-ray machines for detecting flaws or defects in metallic structures are known. A real-time x-ray machine can provide a continuous x-ray image of a structure moving across the x-ray machine's field of view. Conventional real-time x-ray machines are typically based on cartesian motion control systems that allow translational movement of an x-ray source and imaging panel in one or two degrees of freedom relative to the stationary structure being inspected. Such systems are inherently limited in flexibility, and often cannot adequately image all desired areas of complex structures without repositioning of the structures relative to the x-ray source. For large or awkward structures, this repositioning to ensure accurate imaging may prove time consuming and labor intensive. In addition, this repositioning may also require expensive fixturing or heavy-duty motion systems, with different structures requiring different item-specific fixtures.

To maintain the integrity of the resulting x-ray image, conventional x-ray systems typically require that the plane of the imaging panel be perpendicular to, and at least approximately centered on, the x-ray beam axis. Significant problems or difficulties may be encountered if the x-ray source and imaging panel are allowed to move independent of each other off the x-ray beam axis. As one solution to this problem, Xylon Corporation produces a real-time x-ray system having a rigid C-frame that holds the x-ray source and imaging panel in a fixed relationship to each other during motion to ensure proper imaging. The C-frame, however, is only free to translate in two degrees of freedom relative to the part, and thus repositioning of structures is often required for comprehensive x-ray inspections.

When an acceptable flaw or defect is found in a structure through x-ray inspection, it is important to identify the actual location of the defect on the structure so that a subsequent inspection or repair can be effectively carried out. One difficulty with conventional real-time x-ray systems is that the axial location of the defect along the x-ray beam axis may be difficult to ascertain for structures having substantial depth or multiple portions along that axis. For example, when inspecting a circumferential weld around a cylindrical duct where the x-ray beam axis is positioned parallel to the weld plane, it may be difficult to determine if an observed defect in the weld exists on the near side of the duct or the far side of the duct relative to the x-ray source. If the axial location of the defect cannot be sufficiently determined, then either the x-ray machine or the structure must be repositioned for further x-ray imaging in an effort to ascertain the defect's actual location.

The size of defects in metallic parts is often extremely small and non-visible to the human eye. In addition, the lack of reference points on the surface of a structure often make it difficult to correlate the location of a defect as seen on the x-ray image display screen to a precise location on the part. For these reasons, it may be difficult to determine the precise lateral location of a defect on the surface of a part, even when the general axial location of the defect can be ascertained.

By placing a structure for inspection between the x-ray source and the imaging panel, any defect observed will be projected onto the imaging panel in a magnified size. Another difficulty with conventional real-time x-ray systems is that even when the axial and lateral location of the defect can be ascertained, the actual size of the defect is often difficult to determine with any precision because of this geometric magnification. Determining the size of the defect is important, however, as it will dictate either the acceptability of the structure or the nature of the repair which must be carried out. Determination of the defect's size in conventional systems, however, has typically required physical measurements by an operator using manual measuring devices. Not only is this a tedious, labor intensive exercise, but it can also result in a somewhat inexact determination of the size of the defect.

SUMMARY OF THE INVENTION

The present invention provides a real-time, non-destructive inspection system usable to inspect a selected structure for defects. The inspection system is also usable to visually identify a defects location on the structure. One embodiment of the invention provides an articulatable robot arm movable relative to the structure. A movable support system is attached to the articulatable robot arm and has first and second support portions spaced apart from each other defining a space therebetween sized to receive the structure being inspected. An imaging source is attached to the first support portion and is adapted to project an imaging beam along an imaging beam axis. An imaging detector panel is attached to the second support portion and is spaced apart from the imaging source. The imaging detector panel is positioned at least approximately perpendicular to, and intersecting, the imaging beam axis. The imaging source and detector panel are configured to provide images of the structure. A display screen is coupled to the imaging detector panel to display the images of the structure in real-time as the structure is being inspected. Accordingly, the inspection system of the present invention can fully inspect the selected structure by maneuvering the imaging source and imaging detector panel relative to the structure while providing images of the structure to the operator in real-time.

Another embodiment of the invention includes a visual targeting system adjacent to the imaging source and configured to identify where the imaging beam axis intersects the structure undergoing inspection. The visual targeting system in one embodiment has a first line generator positioned adjacent to the imaging source and configured to project a first light plane collinear with the imaging beam axis. A second line generator is also adjacent to the imaging source and configured to project a second light plane collinear with the imaging beam axis and non-parallel to the first light plane. The intersection of the first and second light planes is collinear with the imaging beam axis. In the one embodiment, the intersecting light planes create illuminated cross-hairs that visually indicate the imaging beam axis location on the selected structure to facilitate finding a defect's location on the structure.

Yet another embodiment of the invention provides a method for determining the size of a defect in the selected structure by determining a distance between the imaging source and the defect. The method comprises providing the imaging source in a first source position with an image of the defect on the detector panel being in a first image position. An axial distance between the imaging source and the imaging detector panel is determined when the imaging source is in this first source position. The imaging source is moved to a second source position with the image of the defect on the detector panel being moved laterally to a second image position. The distance moved by the imaging source between the first and second source positions, and the corresponding distance moved by the image of the defect on the detector panel between the first and second image positions, is determined. The distance between the imaging source and the defect is then determined based on the distance between the imaging source and the imaging detector panel, the distance moved by the imaging source, and the corresponding distance moved by the image of the defect. To determine the actual size of the defect, the magnification of the defect's image is determined by the ratio of the distance between the imaging source and the imaging detector panel to the distance between the imaging source and the defect. Accordingly, the size of the defect is then determined by dividing the defect's image size by the magnification of the defect's image.

BRIEF DESCRIPTION OF THE DRAWINGS

FIG. 6 is a schematic top view of the imaging system of FIG. 1 with the imaging source shown in solid lines in a first position and shown in phantom lines in a displaced second position.

FIG. 7 is a front elevation view of the display screen of FIG. 3 showing an image of the defect when the imaging source of FIG. 6 is in the first position.

FIG. 8 is a front elevation view of the display screen of FIG. 3 showing an image of the defect when the imaging source of FIG. 6 is in the second position.

FIG. 12 is a schematic top view of an alternate embodiment of the imaging system of FIG. 1 with the imaging source shown in solid lines in a first position and shown in phantom lines in a displaced second position.

FIG. 13 is a front elevation view of the display screen of FIG. 3 showing an image of the defect when the imaging source of FIG. 9 is in the first position.

FIG. 14 is a front elevation view of the display screen of FIG. 1 showing an image of the defect when the imaging source of FIG. 9 is in the second position.

DETAILED DESCRIPTION

In the following description, certain specific details are set forth in order to provide a thorough understanding of various embodiments of the invention. The present disclosure describes automated real-time, non-destructive inspection systems. The disclosure also describes methods for using the inspection systems in locating selected portions of structures, such as flaws and defects, and determining the size of those portions. Many specific details of certain embodiments of the invention are set forth in the description and in FIGS. 1–11 to provide a thorough understanding of these embodiments. One skilled in the art will understand, however, that the present invention may have additional embodiments, or that the invention may be practiced without several of the details described below. In other instances, well-known structures associated with inspection systems have not been shown or described in detail to avoid unnecessarily obscuring the description of the embodiments of the invention.

Figure 1:
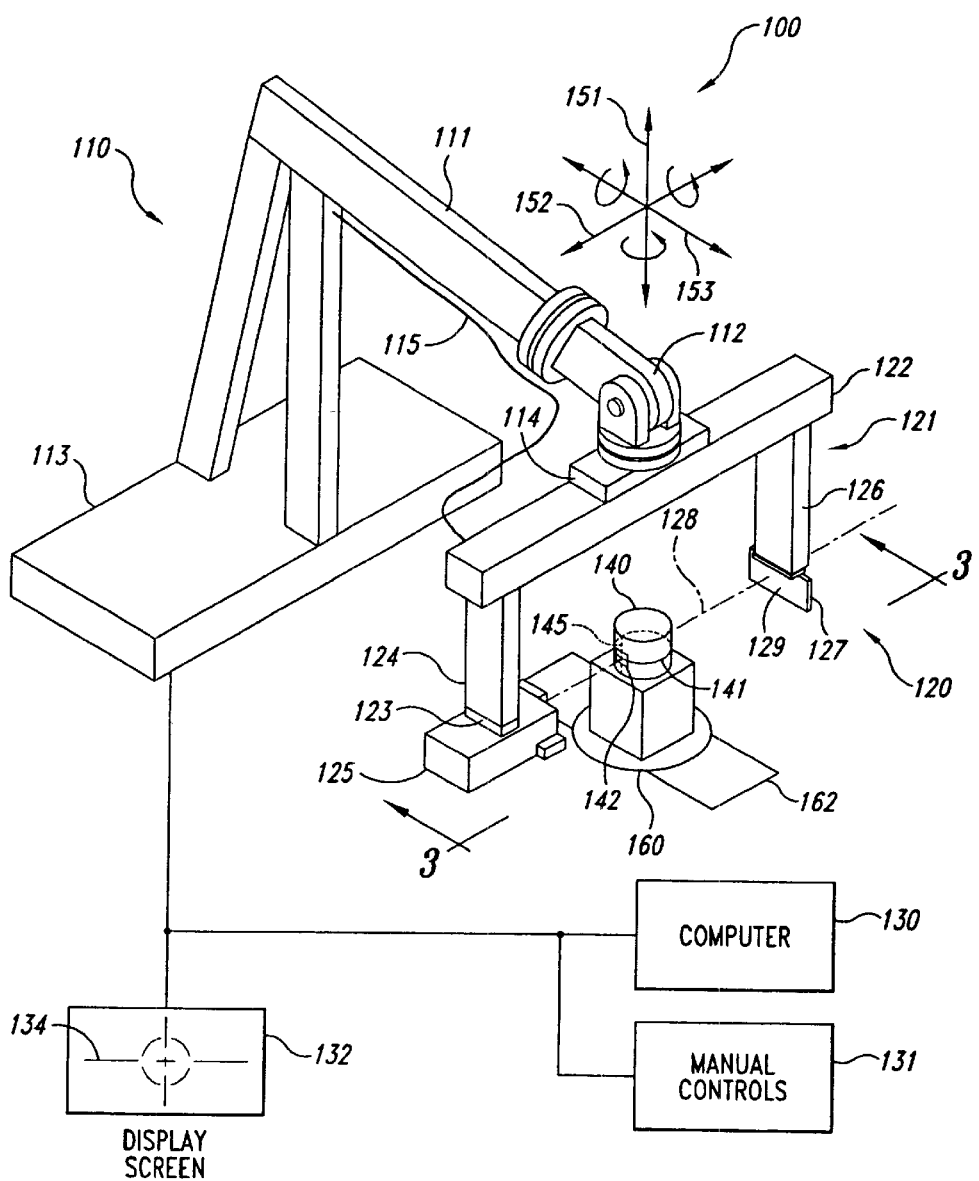
FIG. 1 is an isometric view of an automated real-time, non-destructive inspection system in accordance with an embodiment of the invention.

FIG. 1 is an isometric view of an automated real-time, non-destructive inspection system 100 in accordance with an embodiment of the invention for inspection of a selected structure or structure 140, such as a welded component of a larger assembly. The automated real-time, non-destructive inspection system 100 ("inspection system 100") has an imaging system 120 mounted to a support system 121. The support system 121 is in turn mounted to an articulatable robot 110 configured for movement of the support system, and hence the imaging system 120, relative to the structure 140. A display screen 132 is coupled to the imaging system 120 to graphically display images of the structure 140 in real-time as the structure is being inspected. In one aspect of this embodiment, the structure 140 is held in a stationary position, and the inspection system 100 moves relative to the structure to obtain real-time images of the structure from different angular perspectives. A computer 130 and a manual control system 131 are operatively coupled to the robot 110, the support system 121, and the imaging system 120 so that operation of the robot, support system and imaging system can be effectuated either automatically according to a computer program or manually by an operator.

The imaging system 120 includes an imaging source 125 and a detector panel 127 spaced apart from the imaging source. The imaging source 125 projects an imaging beam, such as an x-ray beam or the like, toward the detector panel 127 along a beam axis 128. The detector panel 127 is positioned along the imaging beam axis 128 a selected distance from the imaging source 125. The detector panel 127 has a planar detector portion 129 oriented substantially perpendicular to the imaging beam axis 128. In one embodiment, the imaging system 120 is an x-ray-imaging system. In one aspect of this embodiment, the x-ray-imaging source 125 is a Hamamatsu 150 KV microfocus x-ray tube, and the detector panel 127 is a Varian VIP-9 amorphous silicon x-ray detector. In other aspects of this embodiment, other x-ray imaging sources 125 and other x-ray detector panels 127, such as amorphous selenium or image intensifiers, may be used. In other embodiments, other types of imaging energy sources that can penetrate the structure 140 may be used as the imaging source 125, including electromagnetic or sonic waves. An imaging energy detector panel should be used that corresponds to the particular type of energy generated by the imaging energy source. For visible and ultraviolet light, charge-coupled device (CCD) cameras may be used. In the case of sonic waves, a vibration-sensitive piezo electric detector may be used as the imaging element in place of the detector panel 127. In yet another embodiment, a heat source may be applied to the structure 140 and infrared video cameras may be used to detect defects in the part.

As best seen in FIG. 1, the imaging system 120 of the illustrated embodiment is mounted on the support system 121. The support system 121 includes a source support arm 124, a track beam 122, and a panel support arm 126. The imaging source 125 is mounted to the source support arm 124 and the detector panel 127 is mounted on the panel support arm 126. Both the source support arm 124 and the panel support arm 126 are movably engaged with the track beam 122 such that their movements are restricted in all directions except along the length of the track beam 122. Accordingly, the imaging source 125 and the detector panel 127 can translate toward or away from each other along an axis 152, but independent lateral motion relative to the support arms and each other is precluded. In an alternate embodiment, however, the imaging source 125 can independently translate laterally relative to the source support arm 124 and the detector panel 127 for short distances along an axis 153 perpendicular to the track beam 122 by way of a roller coupling 123 that movably attaches the imaging source 125 to the source support arm. In another alternate embodiment, the detector panel 127 can be movably attached to the panel support arm 126, such as by a roller coupling or the like, so that the detector panel can also translate laterally relative to the panel support arm and the imaging source 125 in a direction perpendicular to the track beam 122.

The support system 121 of the illustrated embodiment of FIG. 1 is movably coupled to the articulatable robot 110 for movement of the imaging system 120 as a unit relative to the structure 140. The robot 110 includes an articulatable head 112, an articulatable arm 111, and a supporting base 113. A bracket 114 on the track beam 122 mounts the support system 121 to the articulatable head 112, and the articulatable head 112 is in turn movably connected to the articulatable arm 111. In one embodiment, the robot 110 is an ABB6400 250 Kg Wrist Capacity Robot with S4C controller, coupled to an ABB IRTB 6002S robot track. In other embodiments, other suitable robots can be used. A wire harness assembly 115 for transmitting power and data to and from the imaging system 120 is suitably attached to the articulatable arm 111 in such a way that the wire harness will not inhibit movement of the support system 121, the imaging system or the robot 110.

The computer 130 can be used to automatically cool the motion of the robot 110, support system 121, and the imaging system 120 relative to the selected structure 140 being examined. In this embodiment, the computer 130 is configured to control these systems via a suitable computer program or routine. Alternatively, motion of these systems can be accomplished by an operator using the manual controls 131 coupled to the robot 110, support system 121, or imaging system 120. As the imaging system 120 is moved relative to the structure 140, a real-time display of an image of the structure being inspected is provided from the detector panel 127 to the display screen 132, which a user can view during an inspection procedure. In one aspect of this embodiment, the graphical display on the display screen 132 can contain computer-generated cross-hairs 134 (shown in FIG. 1) that represent the location of the imaging beam axis 128 relative to the structure 140 being viewed. In another aspect of this embodiment, the display screen 132 can include two Matrox PC-based frame grabber cards used in conjunction with a Barco 5 megapixel medical grade video display monitor. In other embodiments, other software and other display monitors can be used to provide the real-time display of the structure during inspection.

In one embodiment, a track assembly 162 optionally including a turntable 160 is provided between the source support arm 124 and the panel support arm 126 to support the structure 140 in a selected position relative to the imaging beam axis 128. The track assembly 162 and/or the turntable 160 is configured to move the structure 140 relative to the ground, while the robot 110 moves the imaging system 120 relative to the structure and the ground. The track 162 and/or turntable 160 may be used when translation or rotation, respectively, of the structure 140 relative to the imaging system 120 would facilitate the inspection process. The track 162, oriented, as shown in FIG. 1, would permit the structure 140 to be translated along the axis 153 relative to the ground and the imaging system 120. The track 162 can be oriented at other angles if advantageous. Similarly, rotation of the turntable 160 would permit rotation of the structure 140 about an axis 151 relative to the ground and the imaging system 120. The track 162 and/or turntable 160 can be operatively coupled to the computer 130 for automated structure orientation or to coordinate motion of the structure with motion of the imaging system 120. Use of the track 162 and/or turntable 160 may provide certain advantages for the inspection of larger parts.

The inspection system 100 is capable of moving the imaging system 120 in a full six degrees of motion while providing a real-time image on the display screen 132 of the structure 140 under inspection. The imaging beam axis 128 remains substantially perpendicular to, and generally centered on, the detector panel 127 during such movement. In one aspect of this embodiment, the articulatable head 112 can impart rotation to the imaging system 120 about the axes 151, 152 and 153, respectively. Translation of the imaging system 120 along these axes can be accomplished by movement of the robot 110 and/or the articulatable arm 111 relative to the base 113. As mentioned above, the imaging source 125 and detector panel 127 are also capable of moving toward or away from each other along the track beam 122. It will be apparent to those of skill in the art that the foregoing translational and rotational motions of the imaging system 120 provide a very high degree of control and accuracy to the inspection process.

An understanding of a typical inspection procedure using the inspection system 100 can be gained with reference to FIG. 1 and the following example. To inspect a circumferential weld 141 in the structure 140, for example, the robot 110 positions the imaging system 120 so that the imaging beam axis 128 at least approximately intersects the weld 141. An operator can use the display screen 132 to confirm that the imaging system 120 is properly aligned, as the computer-generated cross-hairs 134 will indicate the location of the imaging beam axis 128 relative to the weld or other portion of the structure 140 being viewed. The robot 110 then moves the imaging system 120 along a prescribed path around the structure 140, the path being selected based upon the areas of the structure being inspected. For example, if the circumferential weld 141 on the structure 140 is being inspected, the robot 110 rotates the imaging system 120 about the axis 151 as the imaging beam axis 128 maintains alignment with the weld 141, until the entire weld 141 has been imaged and inspected. An image of the weld 141 is displayed on the display screen 132 for the operator to view real-time as the imaging system 120 moves around the structure 140. If the image discloses the defect 142, the inspection process can be temporarily stopped while the defect's location is marked on the structure for subsequent inspection or repair. A vertical weld 145 can be similarly inspected by translation of the imaging system 120 along the axis 151. The ability of the inspection system 100 to fully inspect the circumferential weld 141 or the vertical weld 145 obviates the need to reposition the structure 140 at any time during the inspection. As will be apparent to those of skill in the art, virtually any structure orientation can be inspected using the inspection system 100.

Figure 2:
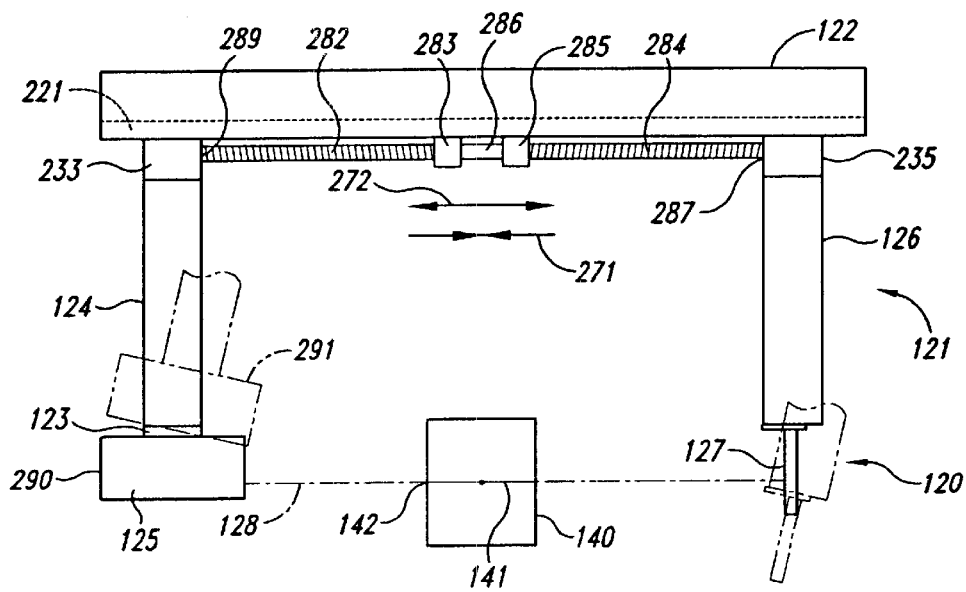
FIG. 2 is an enlarged side elevation view taken substantially along lines 2—2 in FIG. 1 illustrating an imaging system and a support system of the inspection system, the imaging and support systems are shown in solid lines in a first position and are shown in phantom lines in a displaced second position.

FIG. 2 is an enlarged side elevation view of imaging system 120 and the support system 121 taken substantially along lines 2—2 in FIG. 1, in accordance with an embodiment of the invention. A fitting 233 at a top portion of the source support arm 124 extends into an elongated channel 221 running lengthwise in the track beam 122 such that the fitting movably engages the track beam. A fitting 235 on the top portion of the panel support arm 126 similarly extends into the channel 221 and movably engages the track beam. A drive screw 282 mates to a drive motor 283 mounted to the track beam 122, and to a threaded coupling 289 attached to the fitting 233 of the source support arm 124. A drive screw 284 similarly mates to a drive motor 285 mounted to the track beam 122, and to a threaded coupling 287 attached to the fitting 235 of the panel support arm 126.

As mentioned above, the source support arm 124 and the panel support arm 126 can move toward or away from each other as indicated by arrows 271 and 272, respectively. Motion of the source support arm 124 and panel support arm 126 in directions 271 and 272 is effectuated by the drive motors 283 or 285, respectively, turning the drive screws 282 or 284, respectively. In the illustrated embodiment, the drive motors 283 and 285 are synchronized so that the source support arm 124 and panel support arm 126 move simultaneously. The independence of the drive motors 283 and 285, however, allows optional selection of either independent or synchronized motion of the imaging source 125 and the detector panel 127. Alternatively, a coupling 286 can be used to couple the drive screw 282 to the drive screw 284 to permit only synchronized motion of the imaging source 125 and detector panel 127, either together or away from each other. As will be appreciated by those of skill in the art, in an alternate embodiment a single drive motor, for example either drive motor 283 or 285, can be used. In this embodiment, the drive screws 282 and 284 will be coupled together and both driven by the single drive motor to effectuate synchronized motion of the imaging source 125 and detector panel either toward or away from each other along the track beam 122.

In addition to motion along the track beam 122, in an alternate embodiment the imaging source 125 is also capable of limited movement laterally relative to the source support arm 124 in directions perpendicular to the track beam 122 via the roller coupling 123, thereby allowing for lateral adjustment of the imaging source 125 relative to the detector panel 127. Similarly, in an alternate embodiment the detector panel 127 is also capable of limited movement laterally relative to the panel support arm 126 in directions perpendicular to the track beam 122, thereby allowing for lateral adjustment of the detector panel 127 relative to the imaging source 125. Lateral adjustments of either the imaging source 125 or the detector panel 127 can facilitate methods in accordance with embodiments of the invention for determining the distance between the imaging source 125 and the defect 142, as explained in greater detail below.

Figure 3:
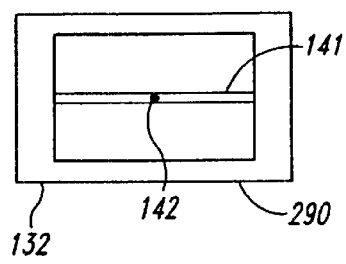
FIG. 3 is a front elevation view of a display screen showing a first image of a selected structure when the imaging system of FIG. 2 is in the first position.
Figure 4:
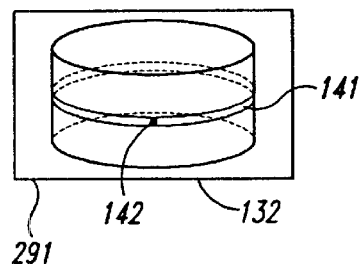
FIG. 4 is a front elevation view of the display screen showing a second image of the selected structure when the imaging system of FIG. 2 in the second position.

FIGS. 3 and 4 are front elevation views of the display screen 132 of FIG. 1 showing images of the structure 140 corresponding to the imaging system of FIG. 2 in two different positions. As best seen in FIG. 2, the structure 140 having the defect 142 is positioned between the imaging source 125 and detector panel 127 for inspection of the weld 141. When the imaging system 120 is in a position so that the plane of the circumferential weld 141 is parallel to the imaging beam axis 128, and as shown in FIG. 3, it may be unclear to an operator whether the defect 142 observed on the display screen 132 is on the part's near side or far side. One way to answer this question using the inspection system 100 is to rotate the imaging system 120 about the axis 153 (FIG. 1) to a selected position, so that the plane of the circumferential weld 141 is no longer parallel to the imaging beam axis 128. As shown in FIG. 4, the circumferential weld 141 will be depicted on the display screen 132 as an ellipse rather than a flat line when the imaging system 120 is at position 291, and the operator should then be able to determine on which side of the structure 140 the defect 142 resides.

Without the ability to move the imaging system 120 in six degrees of motion, many structures would require repositioning in order to afford full inspection. This repositioning could prove an expensive and time-consuming process, particularly for large or awkward structures. One advantage of the inspection system 100 is that it permits complete inspection of a structure without having to stop the inspection process for structure repositioning.

General-purpose robots have benefited from many years of research into the optimum human-machine programming interface. A further advantage of the inspection system 100 is the ability to program all of the required motions of the imaging system 120 into the computer 130, thus eliminating the expense of a human operator. In contrast, conventional x-ray machines with cartesian control systems often require manual control to carry out direct inspections. Programming can also effectively reduce the cost of inspecting large quantities of the same structural configuration, since the same program can be used to inspect all of the structures.

Although the inspection system 100 can be used in the methods explained above in accordance with FIGS. 1–4 to determine the general location of the defect 142 on the structure 140, it is the specific location of the defect that should be marked on the structure so that a subsequent repair can be properly focused. Identifying and marking the specific location of the defect 142 on the structure 140 is not always straightforward. The computer-generated cross-hairs 134 can illustrate on the display screen 132 the position of a defect 142 relative to the imaging beam axis 128. An operator may then be able to see, on the display screen 132 at least, the positional relationship between the defect 142 and the imaging beam axis 128. However, since the imaging beam itself is transparent, the operator will not be able to see where the imaging beam axis 128 actually intersects the structure 140. As a result, the operator may not be able to accurately identify the specific location of the defect 142 on the structure 140 to repair.

Figure 5:
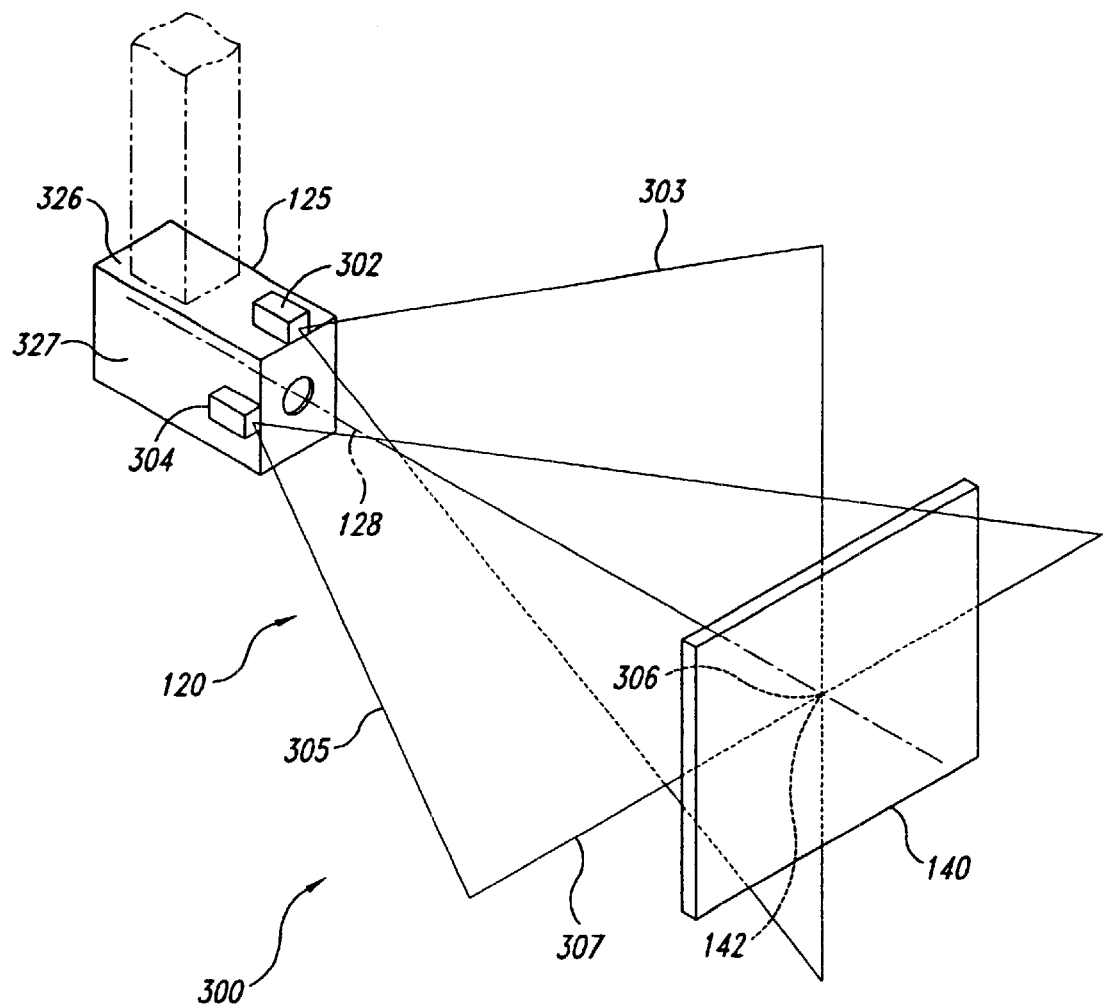
FIG. 5 is an enlarged isometric view of a targeting system of the imaging system of FIG. 1.

FIG. 5 is an isometric view of the imaging system 120 having a targeting system 300 that provides a visual indication on the structure 140 of the specific location of the defect 142, in accordance with an embodiment of the invention. The targeting system 300 includes one line generator 302 mounted on a top surface 326 of the imaging source 125, so that a projected light plane 303 is collinear with and vertically intersects the imaging beam axis 128. The targeting system 300 also includes another, separate line generator 304 mounted to a side 327 of the imaging source 125 so that a projected light plane 305 is collinear with and horizontally intersects the imaging beam axis 128. Accordingly, the intersection of the vertical and horizontal line planes 303 and 305 correspond to the imaging beam axis 128. In one aspect of this embodiment, the line generators 302 and 304 can be Focusable Compact Laser Diode Modules from Edmund Scientific, structure no. F53228. Alternatively, Diffracted Line Generator Optic 60-degree fan angle laser line generators can be used, also from Edmund Scientific stock, structure no. F53759. In yet other embodiments, other suitable light or visible indicia sources can be used.

The targeting system 300 of this embodiment provides illuminated cross-hairs 307 on the structure's outer surface as a visual indication of an intersection 306 of the imaging beam axis 128 with the defect 142 in the structure 140 under inspection. In one aspect of this embodiment, the line generators 302 and 304 are orthogonally mounted relative to each other. In other embodiments, the line generators 302 and 304 can be non-orthogonally mounted relative to each other yet still provide illuminated cross-hairs 307 as a visual indication of the imaging beam axis 128. When the line generators 302 and 304 are non-orthogonally mounted, the respective light planes 303 and 305 can still be positioned collinear with, and intersecting, the imaging beam axis 128 while at a non-orthogonal angle relative to each other. Thus, the light planes 303 and 305 will still project illuminated cross-hairs 307 (albeit non-orthogonal crosshairs) with an intersection collinear with the imaging beam axis 128.

Since the intersection 306 of the illuminated cross-hairs 307 are collinear with the imaging beam axis 128, the operator has a way of visually identifying where the imaging beam axis 128 actually strikes the structure 140 under inspection. By first using the computer-generated cross-hairs 134 on the display screen 132 (FIG. 1) to center the imaging beam axis 128 on the defect 142, the operator can then accurately identify the location of the defect 142 on the structure 140 by marking the spot 306 where the cross-hairs 307 are illuminated on the structure 140. Accordingly, the target system 300 can be used to accurately locate the defect 142 on the structure 140 so that the defect can be further inspected or effectively repaired.

The target system 300 discussed above in accordance with FIG. 5 can provide the lateral position of the defect 142 relative to the imaging beam axis 128. There may be times during the inspection of the structure 140, however, when it will be necessary not only to know the lateral position of the defect 142, but also the axial position of the defect on the structure along the imaging beam axis 128. For example, referring back to FIGS. 2 and 3, an image of the structure 140 taken from position 290 could disclose the lateral position of the defect 142, but would not disclose whether the defect was on the structure's near side, far side, or internal portion. And use of the targeting system 300 would not answer this question. When encountering this situation, one approach as explained above is to maneuver the imaging system 120 while the structure 140 remains stationary, thereby providing another field of view. For example, by rotating the imaging system 120 to position 291 as illustrated in FIGS. 2 and 4. If the operator can then determine the precise location of the defect 142 on the structure 140, the defect can be further inspected or repaired.

While the axial and lateral positions of the defect 142 on the structure 140 may be ascertained by maneuvering the imaging system 120 as shown in FIG. 2 without having to reposition the structure 140, it is also often desirable to accurately determine the size of the defect. The imaging system 120 is configured to determine the actual distance between the imaging source 125 and the defect 142. Once this distance is known, it can be used to determine the magnification of the defect's image as projected onto the imaging panel 127, thereby allowing the size of the defect to be accurately determined.

FIG. 6 is a schematic top view of the imaging system 120 configured for determining the size of the defect 142 by determining a distance $D_{sp}$ between the imaging source 125 and the defect using a method in accordance with an embodiment of the invention. This method requires principally lateral movement of the imaging source 125 relative to the defect 142, as explained above with reference to FIG. 2. The distance $D_{sp}$ between the imaging source 125 and the defect 142 can be determined using the computer 130 (FIG. 1) and Equation (1) below:

$$D_{sp} = \frac{D_{sd} \Delta r_{robot}}{\Delta r_{image} + \Delta r_{robot}} \quad (1)$$

$D_{sp}$ = distance between the imaging source 125 and the defect 142

$D_{sd}$ = distance between the imaging source 125 and the detector panel 127

$\Delta r_{robot}$ = lateral movement of the imaging source 125

$\Delta r_{image}$ = lateral movement of the defect image

The positions of the imaging source 125 and the detector panel 127 on the respective source and panel support arms 124 and 126 are known. Accordingly, the distance $D_{sd}$ between the imaging source 125 and the detector panel 127 is determined via the computer by determining the distance between the source support arm 124 and the panel support arm 126. Alternatively, the distance $D_{sd}$ between the imaging source 125 and the detector panel 127 can be determined and provided to the computer 130 by conventional optical measuring equipment. Once $D_{sd}$ is known, evaluation of Equation (1) for $D_{sp}$ requires knowing a $\Delta r_{robot}$, the lateral distance moved by the imaging source 125 perpendicular to the imaging beam axis 128 between positions 401 and 402; and a $\Delta r_{image}$, the lateral distance moved by the defect's image across the stationary detector panel 127 between positions 412 and 414.

FIGS. 7 and 8 are front elevational views of the display screen 132 illustrating the lateral movement of the defect's image across the stationary detector panel 127 between positions 412 and 414 as needed to calculate $\Delta r_{image}$, in accordance with an embodiment of the invention. A sequence of events that can be used to calculate $\Delta r_{image}$, $\Delta r_{robot}$, and ultimately $D_{sp}$ is as follows: The operator first identifies the defect 142 in the structure 140 being inspected. The defect 142 will be illustrated on the display screen 132 in the first defect image position 412, as shown in FIGS. 6 and 7. The operator then places a cursor on the display screen 132 on an identifiable point 415 of the defect 142, as shown in FIG. 7, and signals the computer 130 to record the first source position 401 of the imaging source 125 relative to the support system 121 (FIG. 1), and the first defect image position 412 of the defect 142 relative to the detector panel 127. The imaging source 125 is then moved laterally relative to the structure 140 to a second source position 402. The operator then places the cursor back on the same identifiable point 415 on the defect 142, as shown in FIG. 8, and signals the computer 130 to record the second source position 402 of the image source 125 relative to the first source position 401, and a second defect image position 414 of the defect 142 relative to the first defect image position 412. Given the four positional data points 401, 402, 412, and 414, the computer 130 determines $\Delta r_{robot}$ and $\Delta_{image}$, and uses them with the known value of $D_{sd}$ to evaluate Equation (1) to calculate $D_{sp}$. In an alternate embodiment, rather than have Equation (1) programmed into the computer 130, $D_{sd}$, $\Delta r_{robot}$ and $\Delta r_{image}$ can be provided on the display screen 132 using suitable software, and Equation (1) can be evaluated by the operator using other computational means.

Once the distance $D_{sp}$ between the imaging source 125 and the defect 142 is known, a magnification of the defect, M, is calculated using Equation (2) below:

$$M = \frac{Dsd}{Dsp} \quad (2)$$

$Dsp$ = distance between the imaging source 125 and the defect 142

$Dsd$ = distance between the imaging source 125 and detector panel 127

Equation (2) shows that the magnification M is equal to the distance $D_{sd}$ between the imaging source 125 and the detector panel 127, divided by the distance $D_{sp}$ between the imaging source and the defect 142. Once the magnification M of the defect 142 is known, the true size of the defect can be automatically calculated by the computer 130 by dividing the size of the magnified image as shown on the display screen 132 (FIGS. 7 or 8) by the magnification M.

Figure 9:
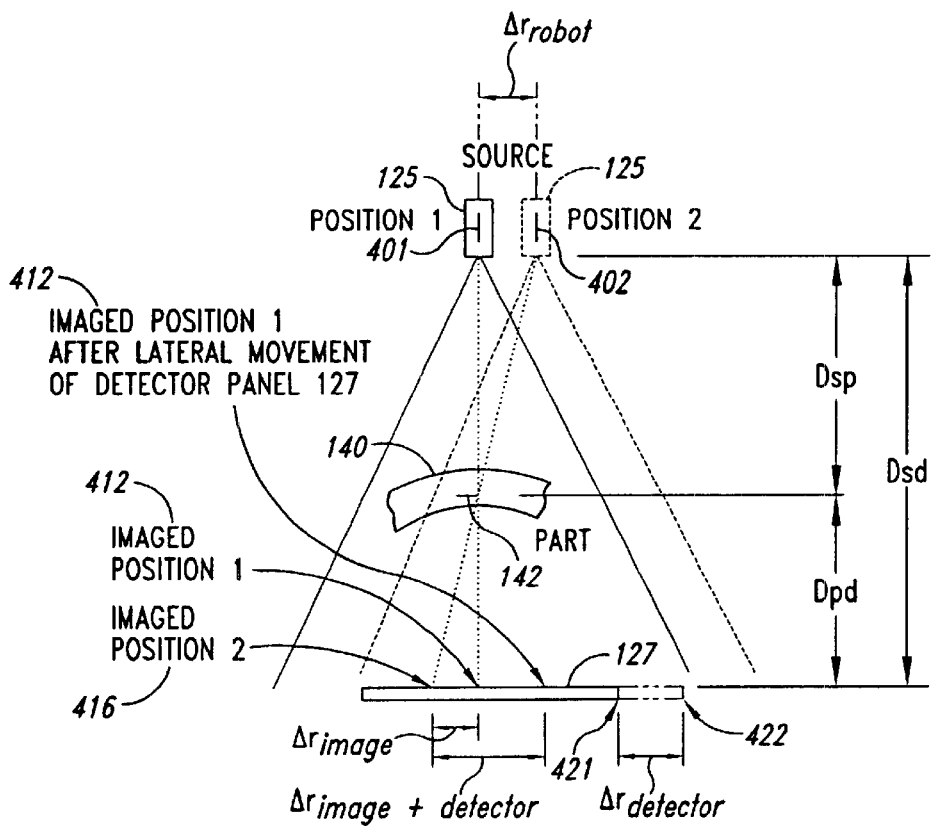
FIG. 9 is a schematic top view of an alternate embodiment of the imaging system of FIG. 1 with the imaging source and detector panel shown in solid lines in first positions and shown in phantom lines in displaced second positions.

FIG. 9 is a schematic top view of the imaging system 120 configured for determining the size of the defect 142 by determining a distance $D_{sp}$ between the imaging source 125 and the defect using a method in accordance with an alternate embodiment of the invention. This method is similar to the method described above in accordance with FIGS. 6–8 except that here the detector panel 127 moves with the imaging source 125 laterally with respect to the defect 142. As a result, this method can be useful when the imaging source 125 and the detector panel 127 are both fixed relative to their respective support arms 124 and 126 such that lateral movement of the imaging source and the detector panel relative to each other is precluded.

The distance $D_{sp}$ between the imaging source 125 and the defect 142 can be determined in this alternate embodiment using Equation (1) as shown above with $D_{sd}$ and $\Delta r_{robot}$ determined as described above. Determining $\Delta r_{image}$ image for use in this embodiment, however, requires taking into account a lateral movement $\Delta r_{detector}$ of the detector panel 127 between a first detector panel position 421, corresponding to the first source position 401, and a second detector panel position 422, corresponding to the second source position 402. As best seen in FIG. 9, the defect image will be in a first defect image position 412 when the detector panel 127 is in the first detector panel position 421, and in a second defect image position 416 when the detector panel is in the second panel position 422.

Figures 10, 11:
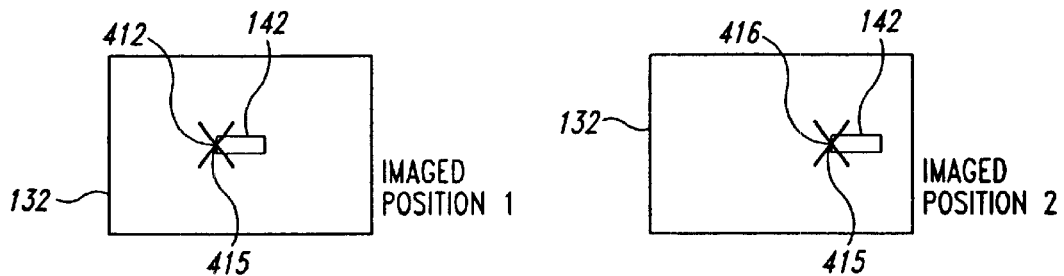
FIG. 10 is a front elevation view of the display screen of FIG. 3 showing an image of the defect when the imaging source and detector panel of FIG. 9 are in their first positions.
FIG. 11 is a front elevation view of the display screen of FIG. 3 showing an image of the defect when the imaging source and detector panel of FIG. 9 are in their second positions.

FIGS. 10 and 11 are front elevational views of the display screen 132 illustrating the lateral movement of the defect's image between positions 412 and 416 as needed to calculate $\Delta r_{image}$. A sequence of events that can be used to calculate $\Delta r_{image}$ in this embodiment is as follows: The operator first identifies the defect 142 in the structure 140 being inspected. The defect 142 will be illustrated on the display screen 132 in the first defect image position 412, as shown in FIGS. 9 and 10. The operator then places a cursor on the display screen 132 on the identifiable point 415 of the defect 142, as shown in FIG. 10, and signals the computer 130 to record the first detector panel position 421 relative to the support system 121 (FIG. 1), and the first defect image position 412 of the defect 142 relative to the detector panel 127. The imaging source 125 and detector panel 127 are then moved laterally relative to the structure 140 to the second source and detector panel positions 402 and 422, respectively. The operator then places the cursor back on the same identifiable point 415 on the defect 142, as shown in FIG. 11, and signals the computer 130 to record the second detector panel position 422 relative to the first detector panel position 421, and the second defect image position 416 of the defect 142 relative to detector panel 127.

Given the two positional data points 421 and 422, the computer 130 can determine the lateral distance $\Delta r_{detector}$ moved by the detector panel 127. Given the two positional data points 412 and 416, the computer 130 can also determine a lateral distance $\Delta r_{image+detector}$ moved by the defect image on the detector panel 127 between positions 412 and 416. The lateral distance $\Delta r_{detector}$ should then be subtracted from the lateral distance $\Delta r_{image+detector}$ to determine $\Delta r_{image}$. Equation (1) above is then evaluated using this value of $\Delta r_{image}$ along with $D_{sd}$ and $\Delta r_{robot}$ to calculate $D_{sp}$. Once the distance $D_{sp}$ between the imaging source 125 and the defect 142 is known, the magnification M of the defect is calculated using Equation (2) above.

FIG. 12 is a schematic top view of the imaging system 120 configured for determining the size of the defect 142 and a distance $D_{sp_1}$ between the imaging source 125 and the defect using alternate methods in accordance with another embodiment of the invention. These methods involve axial movement of the imaging source 125 relative to the detector panel 127 along the track beam 122 as explained above with reference to FIG. 2. The distance $D_{sp_1}$ between the imaging source 125 and the defect 142 can be determined using the computer 130 (FIG. 1) and Equation (3) below:

$$Dsp_1 = \frac{\frac{S_2}{S_1}\Delta Dsp}{1 - \frac{S_2}{S_1}} \quad (3)$$

$D_{sp_1}$ = distance between the imaging source 125 and the defect 142

$\Delta D_{sp}$ = axial movement of the imaging source 125

$S_1$ = first image size of the defect 142

$S_2$ = second image size of the defect 142

Evaluation of Equation (3) for $D_{sp_1}$ requires knowing an axial distance $\Delta D_{sp}$ the imaging source 125 moves between source positions 501 and 502, a first image size $S_1$ of the defect 142, and a second image size $S_2$ of the defect.

FIGS. 13 and 14 are front elevation views of the display screen 132 illustrating first and second image sizes of the defect 142, respectively, in accordance with an embodiment of the invention. Two identifiable points on the defect 142 should be ascertainable to define the first defect image size $S_1$ when the imaging source 125 is in the first source position 501, and to define the second defect image size $S_2$ when the imaging source 125 is in the second source position 502. Two such distinct points can be defined by points 531 and 532 when the imaging source 125 is in the first source position 501, as shown in FIG. 13, and can be defined by points 541 and 542 when the imaging source 125 is in the second source position 502, as shown in FIG. 14.

A sequence of events that can be used to calculate $S_1$, $S_2$, and ultimately $D_{SP_1}$ is as follows: The operator first identifies the defect 142 in the structure 140 being inspected. The operator then sequentially places a cursor on the display screen 132 on the two identifiable points 531 and 532 as shown in FIG. 13, and signals the computer 130 to record the first defect image size $S_1$, and to record the first source position 501 of the imaging source 125 relative to the support system 121 (FIG. 1). The imaging source 125 is then moved axially to the second source position 502, and the operator sequentially places the cursor back on the two identifiable points, now 541 and 542 as shown in FIG. 14, and signals the computer 130 to record the second defect image size $S_2$, and to record the second source position 502 of the imaging source 125 relative to the first source position 501. The imaging source 125 then returns to the first source position 501. The computer 130 now has values for $\Delta D_{sp}$, $S_1$, and $S_2$, the variables required to evaluate Equation (3) for the distance $D_{SP_1}$ between the imaging source 125 at the first source position 501 and the defect 142.

The magnification $M_1$ of the defect 142 is calculated with Equation (4):

$$M_1 = \frac{Dsd\left(1 - \frac{S_2}{S_1}\right)}{\left(\frac{S_2}{S_1}\right)\Delta Dsp} \quad (4)$$

$\Delta D_{sp}$ = axial movement of the imaging source 125
$D_{sd}$ = distance between the imaging source 125 and the detector panel 127
$S_1$ = first image size of the defect 142
$S_2$ = second image size of the defect 142

Evaluation of Equation (4) only requires additionally knowing the distance $D_{sd}$ between the imaging source 125 and the detector panel 127. This value is either already known or readily ascertainable by the computer 130 as discussed above.

By using the inspection system 100 disclosed herein, the structure 140 can be comprehensively and automatically inspected in real-time without requiring repositioning or refixturing of the structure. In addition, the lateral position of the defect 142 can be quickly identified on the surface of the structure 140 using the targeting system 300. Similarly, the axial position of the defect 142 within the structure 140, as well as the size of the defect, can also be accurately ascertained using the methods discussed above in accordance with Equations (1)–(4), allowing the defect to be further examined or repaired as needed. This provides for faster, more efficient, and less labor-intensive inspection of structures which can reduce the overall manufacturing costs. Although specific embodiments, and examples for, the present invention are described herein for illustrative purposes, it will be apparent to those of skill in the art that various equivalent modifications can be made without departing from the spirit and scope of the invention.

The teachings provided herein of the automated real-time, non-destructive inspection system 100 can be applied to other imaging systems in addition to the exemplary x-ray apparatuses and methods described above. In general, in the following claims, the terms used should not be construed to limit the invention to the specific embodiments disclosed in the specification and the claims, but should be construed to include all non-destructive test equipment and methods that operate in accordance with the claims to provide the real-time inspection and location techniques in accordance with the disclosure and claims. Accordingly, the invention is not limited by the disclosure but instead its scope is to be determined entirely by the following claims.

I claim:

1. A method for determining an axial distance between an imaging source and a selected portion of a structure, the structure being positioned between the imaging source and an imaging detector panel spaced apart from the imaging source, the method comprising:

detecting an image of the selected portion on the imaging detector panel when the imaging source is in a first source position;

determining a first image position of the selected portion image on the detector panel when the imaging source is in the first source position;

determining an axial distance between the imaging source and the imaging detector panel when the imaging source is in the first source position;

moving the imaging source laterally relative to the selected portion to a second source position;

determining a lateral distance moved by the imaging source between the first source position and the second source position;

determining a second image position of the selected portion image on the detector panel when the imaging source is in the second source position;

determining a lateral distance moved by the selected portion image on the detector panel relative to the selected portion between the first image position and the second image position; and determining the axial distance between the imaging source and the selected portion based on the axial distance between the imaging source and the imaging detector panel, the lateral distance moved by the imaging source, and the lateral distance moved by the selected portion image on the imaging detector panel.

2. The method of claim 1 wherein detecting an image of the selected portion on the imaging detector panel comprises detecting an x-ray image of the selected portion on an x-ray image detector panel.

3. The method of claim 1 wherein determining the axial distance between the imaging source and the selected portion includes:

determining a product by multiplying the axial distance between the imaging source and the imaging detector panel by the lateral distance moved by the imaging source between the first source position and the second source position; and dividing the product by a sum of the lateral distance moved by the imaging source between the first source position and the second source position plus the lateral distance moved by the selected portion image on the detector panel between the first image position and the second image position.

4. A method for determining an axial distance between an imaging source and a selected portion of a selected structure, the selected structure being positioned between the imaging source and an imaging detector panel spaced apart from the imaging source, the method comprising:

detecting an image of the selected portion on the imaging detector panel when the imaging source is in a first source position;

determining a first image size of the selected portion image when the imaging source is at the first source position;

moving the imaging source axially relative to the selected portion to a second source position;

determining a second image size of the selected portion image when the imaging source is at the second source position;

determining an axial distance moved by the imaging source between the first and second source positions; and determining the axial distance between the imaging source at the first source position and the selected portion based on the first image size, the second image size, and the axial distance moved by the imaging source.

5. The method of claim 4 wherein detecting an image of the selected portion on the imaging detector panel comprises detecting an x-ray image of the selected portion on an x-ray detector panel.

6. The method of claim 4 further comprising:

determining a product by multiplying the axial distance moved by the imaging source by the second image size; and dividing the product by the difference between the first image size and the second image size.

* * * * *